(12) United States Patent
Balducci et al.

(10) Patent No.: US 8,395,767 B2
(45) Date of Patent: Mar. 12, 2013

(54) APPARATUS FOR INSPECTION OF CONCAVE ELEMENTS INCLUDING CONTAINERS OR CAPS

(75) Inventors: Massimo Balducci, Imola (IT); Sanzio Caroli, Imola (IT)

(73) Assignee: Sacmi Cooperativa Meccanici Imola Societa' Cooperativa, Imola (IT)

( * ) Notice: Subject to any disclaimer, the term of this patent is extended or adjusted under 35 U.S.C. 154(b) by 0 days.

(21) Appl. No.: 13/360,031

(22) Filed: Jan. 27, 2012

(65) Prior Publication Data

US 2012/0200849 A1    Aug. 9, 2012

Related U.S. Application Data

(63) Continuation of application No. PCT/IT2010/000345, filed on Jul. 30, 2010.

(30) Foreign Application Priority Data

Aug. 4, 2009  (IT) .............................. RM2009A0420

(51) Int. Cl.
*G01N 21/00* (2006.01)
(52) U.S. Cl. .................................................. 356/240.1
(58) Field of Classification Search ................ 356/240.1
See application file for complete search history.

(56) References Cited

U.S. PATENT DOCUMENTS

| 4,677,473 | A | * | 6/1987 | Okamoto et al. | ............. 348/126 |
|---|---|---|---|---|---|
| 4,972,093 | A | * | 11/1990 | Cochran et al. | .......... 250/559.08 |
| 5,051,872 | A | * | 9/1991 | Anderson | ..................... 362/558 |
| 5,451,773 | A | * | 9/1995 | Triner et al. | ............... 250/223 B |
| 5,604,550 | A | * | 2/1997 | White | .......................... 396/429 |
| 5,661,294 | A | | 8/1997 | Buchmann et al. | |
| 5,923,419 | A | * | 7/1999 | Thomas | ..................... 356/239.4 |
| 6,025,909 | A | | 2/2000 | Juvinall et al. | |
| 6,359,694 | B1 | | 3/2002 | Stredele et al. | |
| 6,885,393 | B2 | * | 4/2005 | Herre | ............................. 348/125 |
| 7,417,725 | B2 | * | 8/2008 | Colle et al. | ................. 356/240.1 |

FOREIGN PATENT DOCUMENTS

| EP | 1710566 | 10/2006 |
|---|---|---|
| WO | 2005103656 | 11/2005 |

OTHER PUBLICATIONS

International Search Report issued on Dec. 8, 2010 in connection with International Application No. PCT/IT2010/000345 filed on Jul. 30, 2010, 4 pages.

* cited by examiner

*Primary Examiner* — Roy M Punnoose
(74) *Attorney, Agent, or Firm* — Gesmer Updegrove LLP

(57) ABSTRACT

The present invention relates to an Apparatus for inspection of concave elements, for detection of contaminations and/or defects, comprising means for lighting a concave element to be subjected to inspection, an image detection unit, such as a camera or like, an optic group and means for processing images acquired by said image detection unit, in order to individuate said contaminations and/or said defects of said concave element, characterized in that said lighting means comprise a first light source, suitable to generate a diffused lighting direct on the concave surface, and a second light source, suitable to generate a grazing lighting directed on the outer lateral surface of said concave element, and in that said optic group is placed so as to detect light emitted by concave surface and transmitting the same to said image detection unit.

9 Claims, 3 Drawing Sheets

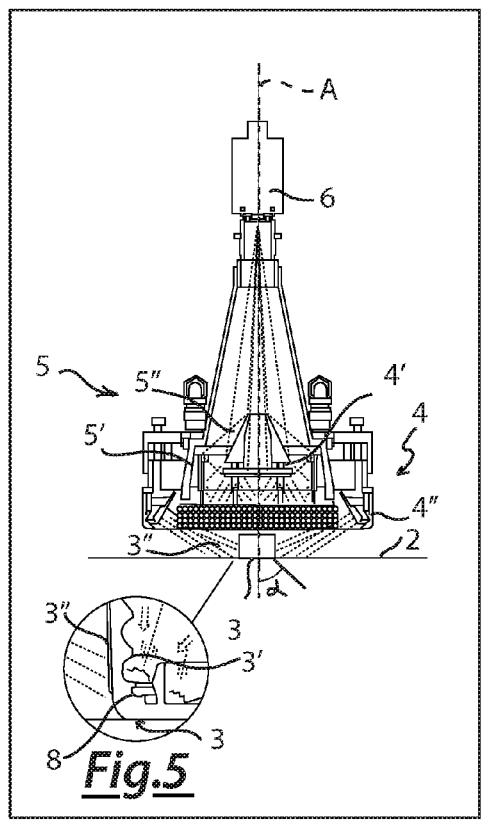
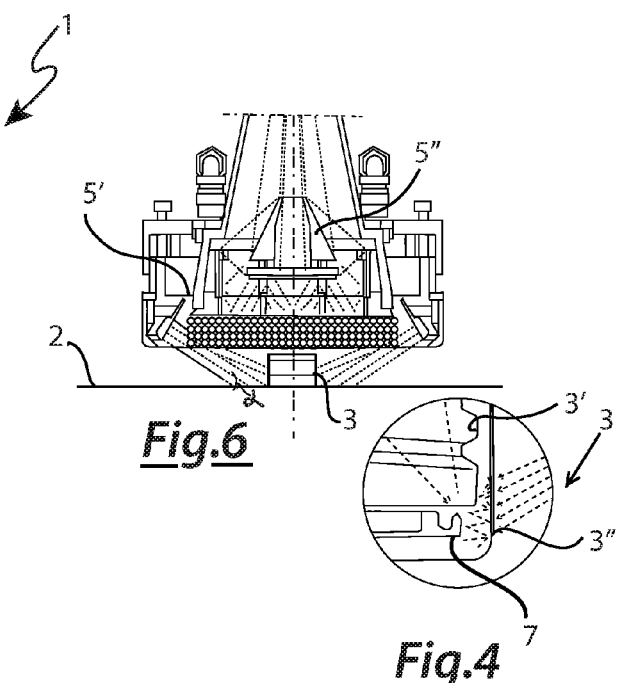
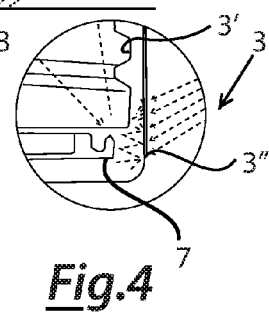
Fig.6
Fig.4
Fig.5
Fig.1
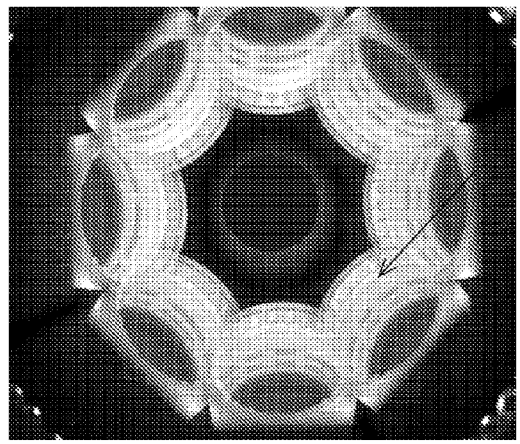
Fig.7

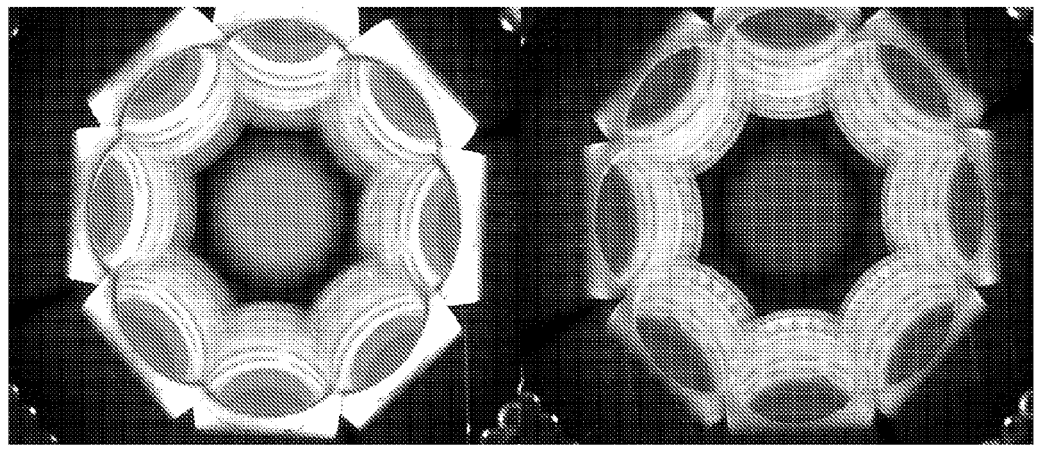
*Fig.8*     *Fig.9*
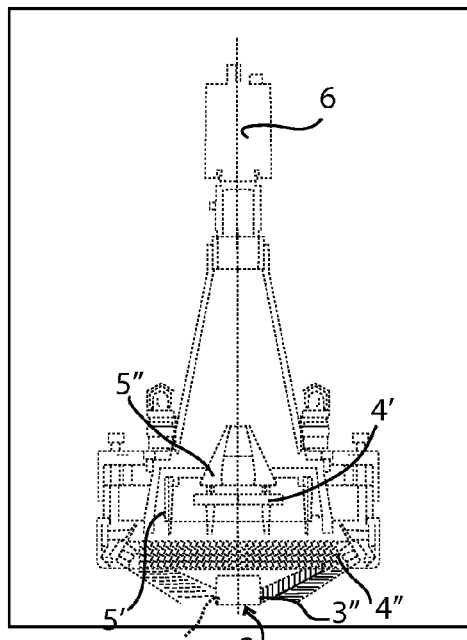
*Fig.2*
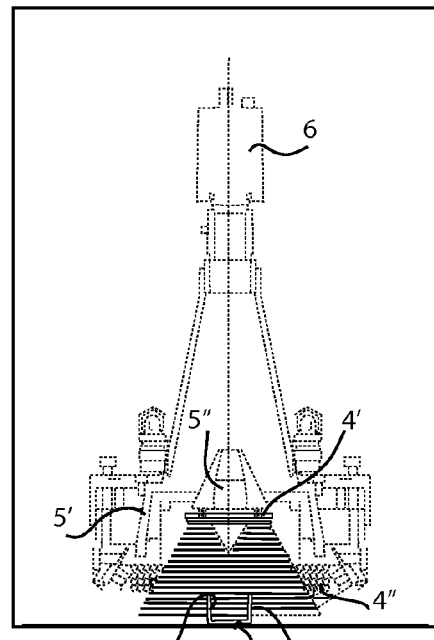
*Fig.3*
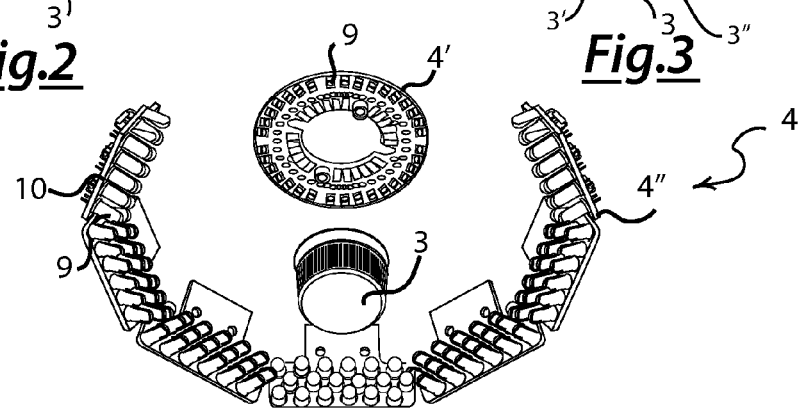
*Fig.10*

APPARATUS FOR INSPECTION OF CONCAVE ELEMENTS INCLUDING CONTAINERS OR CAPS

PRIORITY

The present application is a continuation application of Patent Cooperation Treaty Application PCT/IT2010/00345 filed Jul. 30, 2010, which claims priority to Italian Patent Application RM2009A000420 filed Aug. 4, 2009.

BACKGROUND

The present invention relates to an apparatus for inspection of concave elements, such as containers, caps or like.

More specifically, the invention concerns an apparatus for checking concave elements, and particularly plastic caps, for closing bottles containing soft drinks or like, that can inspect concave surface permitting detection of contaminations and/or defects, such as material exceeding and/or lacking, shape and/or assembling defects.

In the following, the specification will be addressed to the inspection of plastic caps for soft drinks, but it is well evident that the same must not be considered limited to this specific use.

As it is well known, plastic bottles (PET and like) are always more used, said bottles having high hygiene standards and highly reducing transportation expenses, mainly for their reduced weight. Plastic bottles are sealed by suitable caps, coupled by threading. Furthermore, different caps are used on the basis of the beverage contained within the bottle. For carbonated beverages, they are employed caps providing disc-shaped gaskets on the bottom of concave surface, also known as "liners", suitable to limit exit of gas from the bottle. Edge of said gasket is inserted between the cap bottom and a circular relief obtained on the inner lateral surface of the cap, overlapping on said gasket. Instead, caps are used for not carbonated beverages provided with a sealing ring, interacting with the bottle edge.

In this field it is felt the needing of controlling the positioning of the gasket or of the proper shape of the sealing ring, necessary both for ensuring a proper preservation of the product contained within the bottle, and for preventing that beverage can leak additive gas, mainly from the gasket.

At present, different systems exist permitting detecting caps defects, mainly optical systems. Among these solutions it is possible mentioning those described in EP 1078228 B1, JP 9068503, EP 0371547 and JP 2004109064 A, which substantially comprise a camera or sensor, means for lighting the cap to be inspected, an optical group suitable to transmit cap images detected to the camera or sensor lens, so as to obtain an optical representation of said cap. Furthermore, usually, known apparatuses have means for processing images, for automatically detecting cap defects.

However, known systems do not solve the problem of detecting proper positioning of the gasket. Further, optical group used in known apparatuses cannot analyse inner structure of caps, often very complicated.

Finally, due to the always more strict marketing needings, beverage bottles, as well as relevant caps, have different colours. This make difficult maintaining a high reliability level in detecting defects, since contrast between the same cap and the gasket is too low.

SUMMARY

In view of the above, it is therefore object of the present invention that of suggesting an apparatus for inspecting concave elements, such as containers, caps or like, permitting solving the above problems, and particularly detecting both conformation defects of the element subjected to examination, such as the sealing ring in bottle caps, both for complex elements, evaluating possible assembling defects, such as proper positioning of the inner gasket, always when considering caps.

Another object of the present invention is that apparatus according to the present invention is suitable to inspect indifferently caps provided with gasket or sealing ring.

A further object of the present invention is that the apparatus can reliably inspect caps with every colour as well as transparent caps and/or caps opaque to the luminous radiation.

It is therefore specific object of the present invention an apparatus for inspection of concave elements, such as containers, caps or like, for detection of contaminations and/or defects, such as material excess and/or lacks, comprising means for lighting a concave element to be subjected to inspection, an image detection unit, such as a camera or like, an optic group and means for processing images acquired by said image detection unit, in order to individuate said contaminations and/or said defects of said concave element, characterized in that said lighting means comprise a first light source, suitable to generate a diffused lighting direct on the concave surface of said concave element, and a second light source, suitable to generate a grazing lighting directed on the outer lateral surface of said concave element, and in that said optic group is placed so as to detect light emitted by concave surface of said concave element and transmitting the same to said image detection unit.

Always according to the invention, said concave element is opaque to the radiation emitted by said lighting means, said first light source is active, while said second light source is attenuated or switched off, while if said concave element is transparent to radiation emitted by said lighting means, said second light source is active while said first light source is attenuated or switched off.

Still according to the invention, said first light source and said second light source are suitable to generate illuminations with different wavelengths, preferably red and/or blue and/or green and/or infrared, so that if said concave element is transparent to radiation emitted by said lighting means, said lighting means are suitable to illuminate said concave element by a substantially monochromatic light with a wavelength better approaching to the dominant colour of said concave element or with respect to which said concave element is better transparent, while, if said concave element is opaque to radiation emitted by said lighting means, said lighting means are suitable to illuminate said concave element by a substantially monochromatic light with a wavelength better approaching to the dominant colour of the inner parts to be subjected to examination of said concave element, or with respect to which said inner parts are better transparent, or according to a infrared radiation wavelength.

Furthermore, according to the invention, said first light source and said second light source comprise a plurality of LEDs.

Advantageously, according to the invention, said second light source has an annular shape, and said first light source has an annular shape and is placed substantially concentrically with respect to said second light source.

Always according to the invention, said optic group is placed above said concave element to be subjected to inspection and has a detection angle to the outer lateral wall of said concave element, measured with respect to an axis perpendicular with respect to the positioning plane of said concave element to be subjected to inspection, bigger than 30°, preferably about 45°.

Still according to the invention, said optic group comprises a first cylindrical mirror and a second frustum-conical mirror, substantially concentric with respect to said first cylindrical mirror, light emitted by said concave surface of said concave element being reflected by said first cylindrical mirror on said second frustum-conical mirror.

Furthermore according to the invention, said second frustum conical mirror is faceted into eight flat surfaces.

Advantageously according to the invention, said concave element is a cap of the type provided with a gasket or "liner" on the bottom of said concave surface or with a sealing ring.

It is further object of the present invention a method for inspection of concave elements, such as containers, caps or like, for detection of contaminations and/or defects, such as material excess and/or lacks, comprising the following steps: (a) illuminate a concave element to be subjected to inspection; (b) detecting images of said concave element; and (c) processing said detected images in order to individuate said contaminations and/or said defects of said concave element; characterized in that, in said step (a), said concave element is, alternatively or at the same time, lighted, by a diffused lighting component directed on concave surface, and by a grazing lighting component, directed on outer lateral surface of said concave element, and in that, in said step (b), it is detected light emitted by said concave surface of sand concave element.

BRIEF DESCRIPTION OF THE DRAWINGS

The present invention will be now described for illustrative but not limitative purposes according to its preferred embodiments, with particular reference to the figures of the enclosed drawings, wherein:

FIG. 1 shows a schematic section view of apparatus for inspection of concave elements, such as containers, caps or like according to the invention;

FIG. 2 shows lighting of a first light source of apparatus of FIG. 1;

FIG. 3 shows lighting of a second light source of apparatus of FIG. 1;

FIG. 4 shows a detail of lighting of a cap provided with a gasket by apparatus according to FIG. 1;

FIG. 5 shows a detail of lighting of a cap provided with a sealing ring by apparatus according to FIG. 1;

FIG. 6 shows optical path of light globally diffused by a cap under inspection;

FIGS. 7-9 show defects detected on caps by inspection apparatus according to the present invention;

FIG. 10 shows a perspective view of a preferred embodiment of lighting means of inspection apparatus according to the invention.

Similar parts in the different views will be indicated by the same reference numbers.

DETAILED DESCRIPTION

Figure 11:
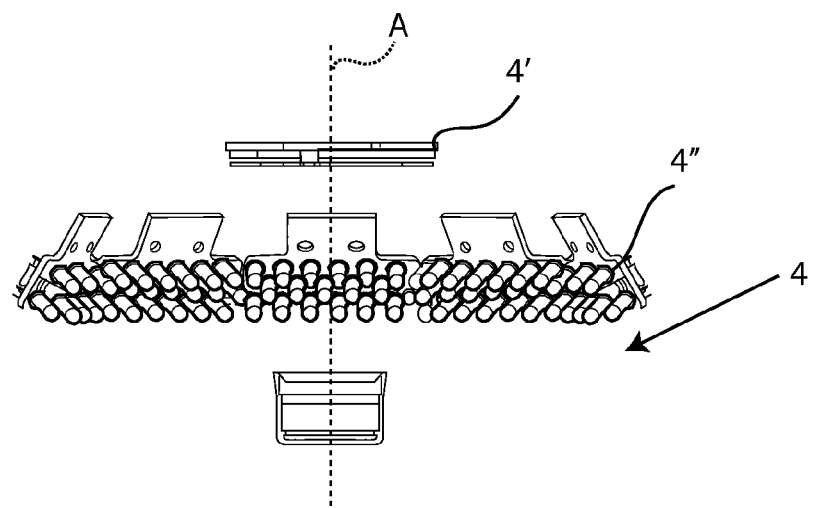
FIG. 11 shows a lateral view of lighting means according to FIG. 10.

Making reference to FIG. 1, it is noted inspection apparatus 1 according to the invention above a conveyor belt 2, on which caps 3 to be subjected to inspection are conveyed, suitably spaced each other. Said caps 3 can be of the type providing a gasket (not shown in the present figure) or of the type provided with sealing ring (not shown in the present figure).

Said apparatus 1 provides lighting means 4 of cap 3, comprising a first light source 4', above said cap 3 to be subjected to inspection, that can generate a diffused light on the concave or inner surface 3' of said cap 3 (see FIG. 2), and a second light source 4", preferably a circular source, provided as well above said cap 3 to be subjected to inspection, suitable to generate a radient lighting directed on lateral surface 3" of said cap 3 (see FIG. 3).

Said inspection apparatus 1 also comprises an optical group 5, above said cap 3, so as to acquire light diffused from concave surface 3' of cap 3 and transmit the same to a camera 6.

Particularly, optical group 5 comprises a first cylindrical mirror 5', and more specifically obtained within inner surface of a cylinder, and a second frustum-conical mirror 5". The latter has a preferably multi-faceted frusto-conical surface, specifically eight flat faces. Said first 5' and second 5" mirrors are provided in such a way to have observation angle α on lateral wall 3" of cap 3 under inspection and control measured with respect to a vertical axis A perpendicular to the plane on which said cap 3 under inspection is positioned (i.e. with respect to the conveyor belt 2 plane) raised with respect to known art, in the order of 45°, differently with respect to a wide-angle lens with a 30° angle. This permit directly observing part of cap 3 contacting the bottle neck, i.e. all the concave surface 3' (comprised of bottom surface of cap 3, on which gasket is placed, and lateral cylindrical surface, on which threading for coupling with bottle neck is provided).

As it can be observed, lighting means 4 are apt to generate a lighting composed by two components, a radient component only on lateral wall and a diffused component on concave surface. They, in combination with optical group 5, can detect light emitted by cap 3 concave surface, permitting detecting defects both for caps 3 with gasket and with sealing ring, and for every cap 3 colour, transparent or opaque to luminous radiation emitted, as it will be better explained in the following.

Particularly, making reference to FIG. 4, in case of a cap 3 with a set transparent colour, provided with a gasket 7, radient component emitted by said second light source 4" lighting the cap 3 on outer surface 3", exploits permeability of plastic to the light. Diffused component is switched off or attenuated. Thus, cap 3 behaves as a diffusing secondary lighting source. Gasket 7 is therefore darker (opaque), since light diffused by the cap 3 must pass through the same, to be then diffused toward optical group 5 and reflected toward camera 6. Therefore, for example in case of exceeding of gasket 7, dark spot would be observed on images detected by camera 6; while in case of gasket 7 lackings, clear areas would be observed.

In case of a cap 3 provided with a sealing ring 8, always a cap 3 with a set colour and transparent to luminous radiation employed (making reference to FIG. 5) operation is the same to the above already described for transparent caps 3 provided with a gasket 7. In this case too, lateral wall 3" of cap 3 lightens thanks to lighting of radient component of second lighting means 4". Ring 8 is darker and in case of holes or lackings, defect will be visible since a clear spot on dark bottom will be visible on image detected by camera 6.

Instead, in case of an opaque cap 3, thus not permeable to luminous or available radiation, provided with gasket 7, diffused component emitted by said first light source 4' is used, while radient component is switched off or attenuated. Said first light source 4' lightens cap 3 from above. In this case, it is gasket 7 which is clearer than cap 3. Therefore, in case of lack of the gasket, a dark part on the cap 3 will be observed on image detected by camera 6, while in case of exceeding material, a clear spot will be detected on the dark background.

For opaque caps, but of the type having a sealing ring 8, said ring 8 will be clearer than the cap 3 wall, so that, lackings, holes or other defects will be observed as dark spots on clear background. Obviously, exceeding material will generate clear spots on dark background.

Apparatus also provides suitable control means (not shown in the figures) for said lighting means 4, connected to said first and to said second light sources 4' and 4" to adjust their operation as described in the above.

FIG. 6 shows in detail optical path 6 of light diffused by said cap 3. Particularly, it is observed that light is subjected to a first reflection on said first mirror 5' and then a second reflection on said second mirror 5". The latter transmits image of the cap 3 to the lens of said camera 6.

FIGS. 7-9 show images detected by camera 6, showing eight cloves of cap 3 under inspection, exactly as faceting of flat surfaces of the second mirror 5". Said images are transmitted to means for processing images (not shown in the figures) that can individuate contaminations and/or defects of the cap 3 under examination. Also detected defects can be observed in said figures, indicated by arrows, and particularly:

in FIG. 7 a lack of matter is indicated;
instead, in FIG. 8 it is indicated a hole; and
in FIG. 9 it is indicated a matter exceeding.

Finally, FIGS. 10 and 11 show a preferred embodiment of lighting means 4, wherein said first light source 4' is realised as a LED circular plane matrix 9, having blue, red and green colours, fixed to a printed board 8. At the same way, said second light source 4" is realised by a plurality of printed boards 10, on which LED diodes 7 are fixed, always blue, red and green LEDs, circularly arranged thus realising a ring. Said printed boards 10 are also provided inclined, to better lighten lateral wall 3" of cap 3, or of other concave element.

Usually, gasket of caps 3 can be of a transparent blue colour, or grey/white opaque colour or of a neutral transparent colour. Caps 3 can be of every colour/e.g. fuchsia, transparent red, purple, silver, gold, green, dark blue, blue, ecc.).

Using white light with a black and white camera 6 (or even with a colour camera), some colour coupling between gasket and cap (e.g. blue/green, blue/silver, blue/gold) give flat images without any contrast. Instead, using monochromatic light (red or green or blue or eventually infrared light), contrast remarkably and generically increases, for caps permeable to light, i.e. transparent, colour chosen for light source is the one more approaching to prevalent colour of the cap 3, in other words, for orange caps it is used red colour, for purple caps it is used red or blue colour. Instead, in case of opaque caps 3, colour chosen for light source is the one more approaching the prevailing colour of the gasket (usually blue or green on coloured gaskets, red or all other components of caps having a neutral or grey or white colour).

Obviously, colours can be mixed, choosing them differently for radient and diffused lighting. Furthermore, it is possible using a colour camera 6 that can separate images obtained by different source colours. In case of opaque caps 3, wherein light can only partially filter, it is also possible using infrared light LEDs 7, having a higher penetration into plastic.

The present invention has been described for illustrative, but not limitative, purposes, according to its preferred embodiments, but it is to be understood that variations and/or modifications can be introduced by those skilled in the art without departing from the relevant scope as defined in the enclosed claims.

The invention claimed is:

1. Apparatus for inspection of concave elements, including containers and/or caps, for detection of contaminations and/or defects, including material excess and/or lacks, comprising
   means for lighting a concave element to be subjected to inspection,
   an image detection unit,
   an optic group and
   means for processing images acquired by said image detection unit, in order to individuate said contaminations and/or said defects of said concave element,
   characterized
   in that said lighting means comprise a first light source, configured to generate a diffused lighting direct on the concave surface of said concave element, and a second light source, configured to generate a grazing lighting directed on the outer lateral surface of said concave element, and
   in that said optic group is placed so as to receive light emitted by concave surface of said concave element and transmitting the same to said image detection unit,
   in such way that
   if said concave element is opaque to the radiation emitted by said lighting means, said first light source is active, while said second light source is attenuated or switched off,
   while, if said concave element is transparent to radiation emitted by said lighting means, said second light source is active while said first light source is attenuated or switched off.

2. Apparatus according to claim 1, characterized in that said first light source and said second light source are suitable to generate illuminations with different wavelengths, preferably red and/or blue and/or green and/or infrared, so that
   if said concave element is transparent to radiation emitted by said lighting means, said lighting means are suitable to illuminate said concave element by a substantially monochromatic light with a wavelength better approaching to the dominant colour of said concave element or with respect to which said concave element is better transparent,
   while, if said concave element is opaque to radiation emitted by said lighting means, said lighting means are suitable to illuminate said concave element by a substantially monochromatic light with a wavelength better approaching to the dominant colour of the inner parts to be subjected to examination of said concave element, or with respect to which said inner parts are better transparent, or according to an infrared radiation wavelength.

3. Apparatus according to claim 1, characterized in that said first light source and said second light source comprise a plurality of LEDs.

4. Apparatus according to claim 1, characterized in that said second light source has an annular shape, and said first light source has an annular shape and is placed substantially concentrically with respect to said second light source.

5. Apparatus according to claim 1, characterized in that said optic group is placed above said concave element to be subjected to inspection and has a detection angle (a) to the outer lateral wall of said concave element, measured with respect to an axis (A) perpendicular with respect to the positioning plane of said concave element to be subjected to inspection, bigger than 30°, preferably about 45°.

6. Apparatus according to claim 1, characterized in that said optic group comprises a first cylindrical mirror and a second frustum-conical mirror, substantially concentric with respect to said first cylindrical mirror, light emitted by said concave surface of said concave element being reflected by said first cylindrical mirror on said second frustum-conical mirror.

7. Apparatus according to claim 1, characterized in that said second frustum conical mirror is faceted into eight flat surfaces.

8. Apparatus according to claim 1, characterized in that said concave element is a cap of the type provided with a gasket or liner on the bottom of said concave surface or with a sealing ring.

9. Method for inspection of concave elements, including containers and/or caps, for detection of contaminations and/or defects, including material excess and/or lacks, comprising the following steps:

(a) illuminate a concave element to be subjected to inspection;
(b) detecting images of said concave element; and
(c) processing said detected images in order to individuate said contaminations and/or said defects of said concave element;

characterized in that, in said step (a), said concave element is, alternatively or at the same time, lighted, by a diffused lighting component directed on concave surface, and by a grazing lighting component, directed on outer lateral surface of said concave element, and in that, in said step (b), the detected images are provided by light emitted by said concave surface of said concave element.

* * * * *